United States Patent
Noshadi

(10) Patent No.: US 11,389,583 B2
(45) Date of Patent: Jul. 19, 2022

(54) BIOCOMPATIBLE OXYGEN GAS GENERATING DEVICES FOR TISSUE ENGINEERING

(71) Applicant: Rowan University, Glassboro, NJ (US)

(72) Inventor: Iman Noshadi, Haddon Heights, NJ (US)

(73) Assignee: Rowan University, Glassboro, NJ (US)

( * ) Notice: Subject to any disclaimer, the term of this patent is extended or adjusted under 35 U.S.C. 154(b) by 246 days.

(21) Appl. No.: 16/869,751

(22) Filed: May 8, 2020

(65) Prior Publication Data

US 2020/0353156 A1    Nov. 12, 2020

Related U.S. Application Data

(60) Provisional application No. 62/844,821, filed on May 8, 2019.

(51) Int. Cl.
*A61L 27/52* (2006.01)
*A61M 5/00* (2006.01)
(Continued)

(52) U.S. Cl.
CPC .......... *A61M 5/00* (2013.01); *A61L 27/3834* (2013.01); *A61L 27/52* (2013.01); *A61L 27/58* (2013.01);
(Continued)

(58) Field of Classification Search
CPC .......... C08L 33/12; C08L 71/02; A61L 27/16; A61L 27/18; A61L 31/048; A61L 31/06; A61L 27/025; A61L 27/08; A61L 27/222; A61L 27/3804; A61L 27/3834; A61L 27/50; A61L 27/52; A61L 27/58; A61L 31/005; A61L 31/024; A61L 31/028; A61L 31/045; A61L 31/14; A61L 31/145; A61L 31/148; A61M 1/1678; A61M 1/32; A61M 2202/0208; A61M 2207/00; A61M 5/00; B82Y 30/00; B82Y 40/00; C25B 11/04; C25B 1/02; C25B 9/17; H01G 11/08; H01G 11/22; H01G 11/54; H01G 9/004; H01M 10/0436; H01M 10/05; H01M 2004/023; H01M 2300/0082; H01M 4/131; H01M 4/133; H01M 4/136; H01M 4/362; H01M 4/5825; H01M 4/583
See application file for complete search history.

(56) References Cited

FOREIGN PATENT DOCUMENTS

WO        2017117467 A1      7/2017

OTHER PUBLICATIONS

Abdi, et al., "An enzyme-modulated oxygen-producing microsystem for regeneratrive therapeutics", Intl J Pharma, vol. 409, Issues 1-2, May 16, 2011, pp. 203-205.
(Continued)

*Primary Examiner* — Ernst V Arnold
(74) *Attorney, Agent, or Firm* — Saul Ewing Arnstein & Lehr LLP; Domingos J. Silva; Dennis Ostrovsky

(57) ABSTRACT

The present invention relates to novel biocompatible oxygen gas generating devices that can be implanted into a living subject. In certain embodiments, the oxygen gas generating devices can be used to deliver oxygen gas to tissue in a subject, thereby stimulating tissue growth and repair. In other embodiments, the devices operate by electrolytically splitting endogenous water in a subject. In yet other embodiments, the device further comprises an implantable supercapacitor capable of supplying energy to the oxygen gas generating device.

26 Claims, 9 Drawing Sheets

(51) Int. Cl.
| | |
|---|---|
| A61L 31/14 | (2006.01) |
| A61L 27/38 | (2006.01) |
| H01M 4/58 | (2010.01) |
| H01M 4/583 | (2010.01) |
| A61L 27/58 | (2006.01) |
| A61M 1/16 | (2006.01) |
| C25B 1/02 | (2006.01) |
| C25B 11/04 | (2021.01) |
| H01G 9/004 | (2006.01) |
| C25B 9/17 | (2021.01) |
| H01M 4/02 | (2006.01) |

(52) U.S. Cl.
CPC .......... *A61L 31/145* (2013.01); *A61L 31/148* (2013.01); *A61M 1/1678* (2013.01); *C25B 1/02* (2013.01); *C25B 9/17* (2021.01); *C25B 11/04* (2013.01); *H01G 9/004* (2013.01); *H01M 4/583* (2013.01); *H01M 4/5825* (2013.01); *A61M 2202/0208* (2013.01); *A61M 2207/00* (2013.01); *H01M 2004/023* (2013.01); *H01M 2300/0082* (2013.01)

(56) References Cited

OTHER PUBLICATIONS

Camci-Unal et al., "Oxygen-releasing biomaterials for tissue engineering", Polym Intl, vol. 62, No. 6, Jun. 1, 2013, pp. 843-848.

Lee, et al., "Controlling oxygen release from hollow microparticles for prolonged cell survival under hypoxic anvironment". Biomater, vol. 53, Jun. 2015, pp. 583-591.

Li, et al., "An oxygen release system to augment cardiac progenitor cell survival and differentiation under hypoxic condition", Biomater, vol. 33, Issue 25, Sep. 2012, pp. 5914-5923.

Liu et al., "Water splitting—biosynthetic system with CO2 reduction efficiencies exceeding photosynthesis", Science, vol. 352, Issue 6290, Jun. 2, 2016, pp. 1210-1213.

Noshadi, et al., "Engineering Biodegradable and Biocompatible Bio-ionic Liquid Conjugated Hydrogels with Tunable Conductivity and Mechanical Properties", Sci Rep, vol. 7, Article No. 4345, Jun. 28, 2017, pp. 1-18.

Pedraza, et al., "Preventing hypoxia-induced cell death in beta cells and islets via hydrolytically activated, oxygen-generating biomaterials", Proc Nat Acad Sci, vol. 109, No. 11, Mar. 13, 2012, pp. 4245-4250.

Wang, et al., "Oxygengenerating nanofiber cell scaffolds with antimicrobial properties", ACS Appl Mater Interfaces, vol. 3, No. 1, Dec. 14, 2010, pp. 67-73.

Ward, et al., "Oxygen generating biomaterials preserve skeletal muscle homeostasis under hypoxic and ischemic conditions", PLoS One, vol. 8, No. 8, Aug. 26, 2013, pp. e72485.

White, et al., "Addition of perfluorocarbons to alginate hydrogels significantly impacts molecular transport and fracture stress", J Biomed Mater Res A, vol. 101, No. 2, Feb. 2013, pp. 438-446.

White, et al., "Perfluorocarbons enhance oxygen transport in alginatebased hydrogels", Polym Adv Technol, vol. 25, Issue 11, Nov. 2014, pp. 1242-1246.

BIOCOMPATIBLE OXYGEN GAS GENERATING DEVICES FOR TISSUE ENGINEERING

CROSS-REFERENCE TO RELATED APPLICATION

This application claims priority to U.S. Provisional Patent Application Ser. No. 62/844,821 entitled "BIOCOMPATIBLE OXYGEN GAS GENERATING DEVICES FOR TISSUE ENGINEERING," filed May 8, 2019, the disclosure of which is incorporated herein by reference in its entirety.

BACKGROUND OF THE INVENTION

Some of the most significant difficulties facing the area of organ transplantation today are the shortage of donor organs, the high cost of transplantation, the unpredictability of transplantation surgeries, and the need for life-long use of immunosuppression. These issue can be addressed by the bioengineering of organ substitutes. A grand challenge that has prevented clinical translation of this technology is that the engineering of organ-sized tissues often results in anoxia-induced cell death, which causes rapid implant failure upon implantation.

Hypoxia (<5% oxygen gas) and anoxia (<0.5% oxygen gas) occur if the distance between cells and blood vessels is more than 100-200 µm. Although hypoxia stimulates angiogenesis and orchestrates metabolic coping mechanisms, anoxia hinders angiogenesis and drives tissue necrosis. Specifically, anoxia prevents aerobic respiration and production of adenosine triphosphate, eventually resulting in cellular death. Anoxia also destroys vascularization networks, which exacerbates the local oxygen gas shortage. Pancreatic cells (($\beta$ cells), muscle cells, hepatocytes, and neurons require a larger amount of oxygen gas and are very sensitive to hypoxic conditions. Anoxic zones can originate in implanted engineered tissues larger than a few millimeters, which become progressively more dominant when increasing the implant size. Consequently, large engineered tissues need to be actively supplied with oxygen gas in a gradual and consistent manner for several days to weeks in order to enable the implant's survival until vascularization of the tissue has occurred.

Several attempts have been made to develop systems to supply oxygen gas to cells of damaged tissues. These include the usage of angiogenic factors (which provides oxygen gas only when vascularization has occurred), implantation adjacent to vascular-rich tissues (which still suffers from diffusion limitations), and oxygen gas carriers such as oxygen gas-rich fluids like perfluorocarbons (PFCs), silicone oils, and crosslinked hemoglobin (which can release oxygen gas only for a few hours).

Some recent strategies have entailed the design of oxygen gas releasing biomaterials (ORBs). ORBs offer localized oxygen gas delivery to engineered tissues via hydrolysis of solid peroxides such as sodium percarbonate, calcium peroxide, and magnesium peroxide. Solid peroxides rapidly decompose upon exposure to water to release oxygen gas, which results in a relatively short (hours to a few days) and unstable (rapidly declining) bulk release of oxygen gas. A significant concern with ORBs is their hydrogen peroxide-based production of reactive oxygen species (ROS) in addition to the salts that are deposited as decomposition byproducts, both of which are known to be cytotoxic. While recent strategies have achieved partial success at short term oxygenation, the challenge of supplying adequate oxygen gas until neovascularization has remained unsolved. Thus, at present, there is no effective strategy to remedy the anoxic environments in vascular destroyed areas or pre vascular implants.

There remains a need in the art for effective in vivo methods of supplying oxygen gas to organs and tissues in a subject. In certain embodiments, the methods involve the use of a biocompatible oxygen gas generating device. The present invention meets these needs.

BRIEF SUMMARY OF THE INVENTION

In certain embodiments, an implantable oxygen generating device is provided. The oxygen generating device includes an oxygen generating, biocompatible electrochemical cell, wherein the electrochemical cell comprises a biocompatible cathode, a biocompatible anode, and a biocompatible hydrogel electrolyte, and wherein the hydrogel electrolyte is in electrochemical contact with the anode and the cathode of the cell. The implantable oxygen generating device also includes a biocompatible power source, wherein the power source is a supercapacitor comprising a plurality of biocompatible electrodes and a biocompatible hydrogel electrolyte, and wherein the hydrogel electrolyte is in electrochemical contact with each of the plurality of the biocompatible electrodes of the power source, wherein the biocompatible hydrogel electrolyte in the cell and the biocompatible hydrogel electrolyte in the power source are independently an electrically conductive hydrogel comprising a biopolymer backbone to which an ionic liquid side chain is conjugated, and wherein the electrochemical cell is in electronic communication with the power source.

In certain embodiments, an oxygen generating biocompatible device is provided. The oxygen generating biocompatible device includes a biocompatible electrochemical cell comprising a graphene hydrogel/cobalt-phosphorous (GH/Co—P) alloy cathode, a graphene hydrogel/cobalt phosphate (GH/CoP$_i$) anode, and a biocompatible, conductive hydrogel electrolyte, wherein the anode and the cathode further comprise silica nanoparticles/laponite, and wherein the hydrogel electrolyte is in electrochemical contact with the biocompatible anode and the biocompatible cathode. The an oxygen generating biocompatible device also includes a power source comprising a plurality of electrodes comprising a graphene hydrogel and laponite, the biocompatible conductive hydrogel electrolyte wherein each of the plurality of electrodes is in electrochemical contact with a biocompatible conductive hydrogel electrolyte, wherein the biocompatible electrochemical cell and the power source are in electronic communication with each other; and wherein each biocompatible conductive hydrogel electrolyte is independently an electrically conductive hydrogel comprising a biopolymer backbone to which an ionic liquid side chain is conjugated.

BRIEF DESCRIPTION OF THE FIGURES

For the purpose of illustrating the invention, depicted in the drawings are certain embodiments of the invention. However, the invention is not limited to the precise arrangements and instrumentalities of the embodiments depicted in the drawings.

FIG. 1B confirms the conjugation of BILs to the GelMA hydrogel.

FIG. 2A shows the effect of BILs conjugation (0-20% w/v) on conductivity of GelMA/BIL. FIG. 2B shows the effect of BILs conjugation (0-20% w/v) on electrochemical potential generation in an electrochemical cell using GelMA/BIL as electrolyte. FIG. 2C shows the effect on the compressive modulus of the GelMA/BIL from changing the BILs concentration (0-20% w/v).

FIG. 3A is a graph showing change in swelling ratio (%) by varying BILs concentration from 0 to 10 (% w/v) (Time:0-24 h). FIG. 3B is a graph showing change degradation ratio of GelMA/BIL by varying BILs concentration from 0-10 (% w/v) (Day 1-14).

FIG. 4A shows representative live/dead images from CMs/CFs encapsulated in GelMA/BIL hydrogels at days 5 post encapsulation. FIG. 4B shows representative F-Actin/DAPI fluorescent images of CMs/CFs encapsulated in GelMA/BIL hydrogels, at days 7 post-encapsulation (scale bar=25 μm). FIG. 4C is an immunofluorescent staining of sarcomeric a-actinin expressed by CMs seeded on GelMA/BIL hydrogels on day 7 (scale bar=25 μm).

FIG. 9A is an image of a GH hydrogel after synthesis. FIG. 9B is a CV curve for a GH electrode at various scan rates (10-200 mV/s). FIG. 9C is a graph showing specific capacitance properties of the GH electrode at various scan rate (10-200 mV/s). FIG. 9D is a graph showing the electrochemical stability of the GH hydrogel.

FIG. 11A is an image of a 3D direct ink printing of GelMA/BILs on a surface. FIG. 11B is a scheme showing a process for fabricating soft solid-state supercapacitors of the invention. FIGS. 11C-11F are images of 3D printed soft solid-state supercapacitors. GH/SNP bio-ink was used as the electrode and GelMA/BIL (20% w/v GelMA and 20% w/v BILs) was used as the electrolyte.

DETAILED DESCRIPTION OF THE INVENTION

Figures 1A, 1B:
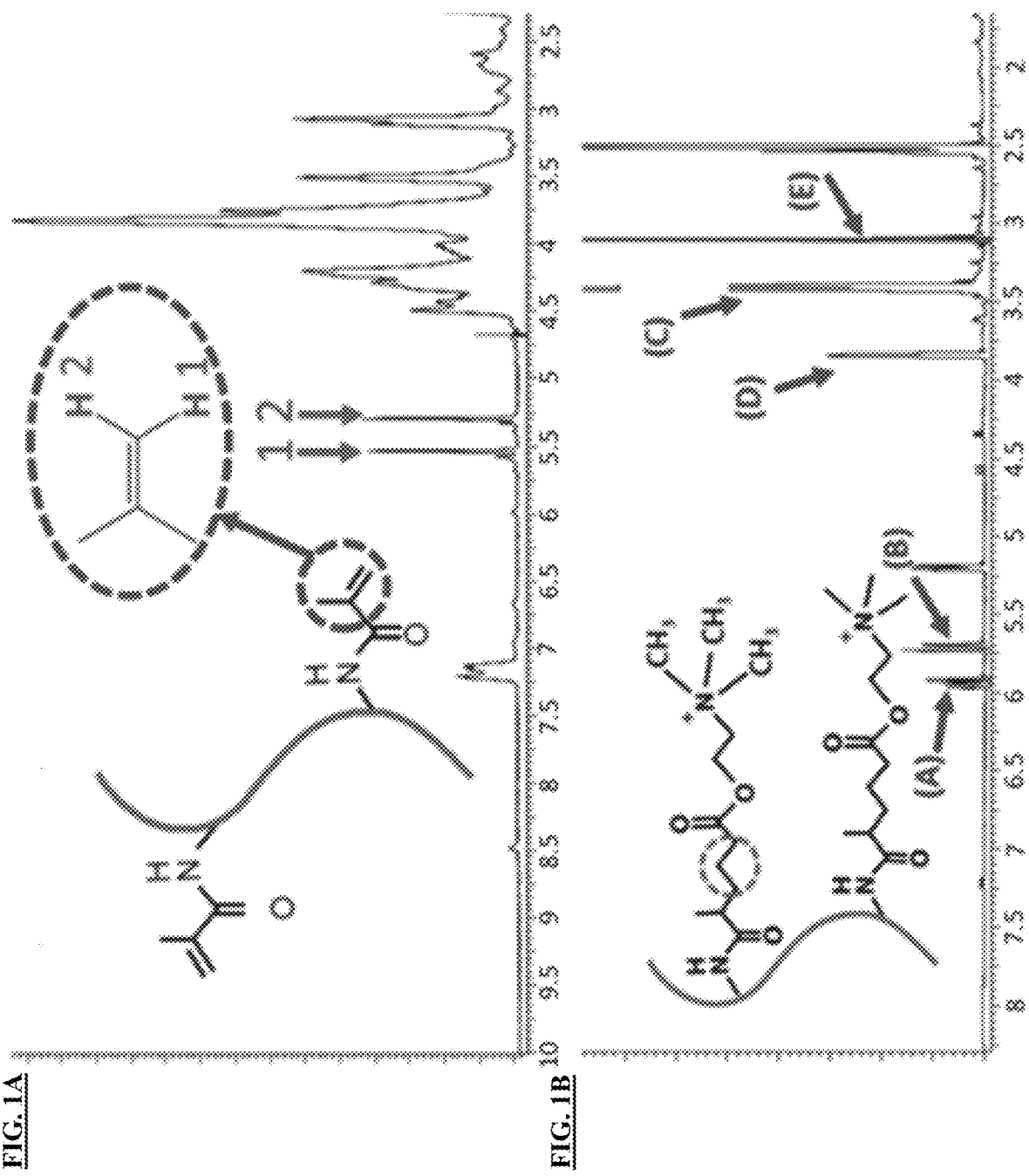
FIGS. 1A-1B show $^1$H-NMR analyses of (FIG. 1A) GelMA prepolymer, and (FIG. 1B) GelMA-BILs.
Figures 2A, 2B, 2C:
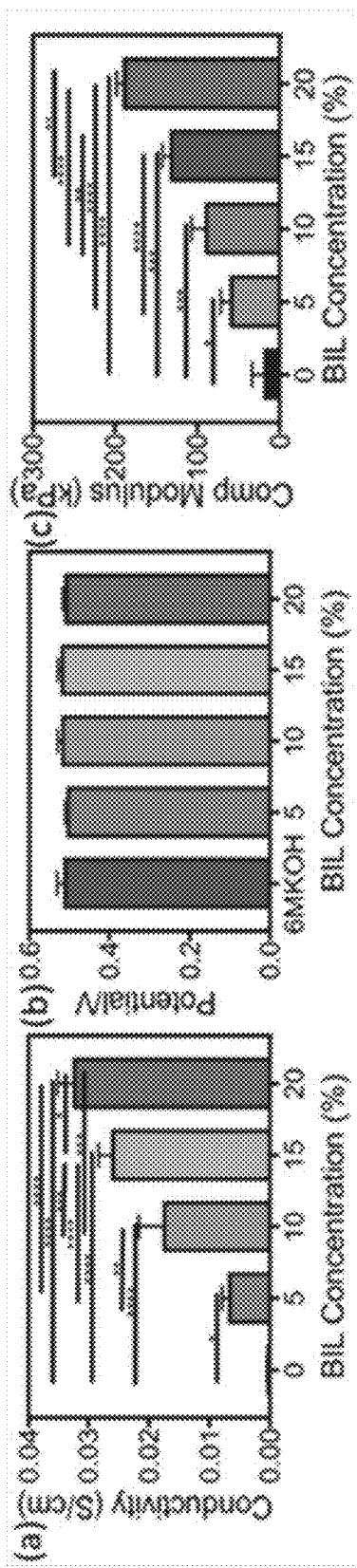
FIGS. 2A-2C are graphs showing electrical and mechanical properties of the GelMA/BIL.
Figures 3A, 3B:
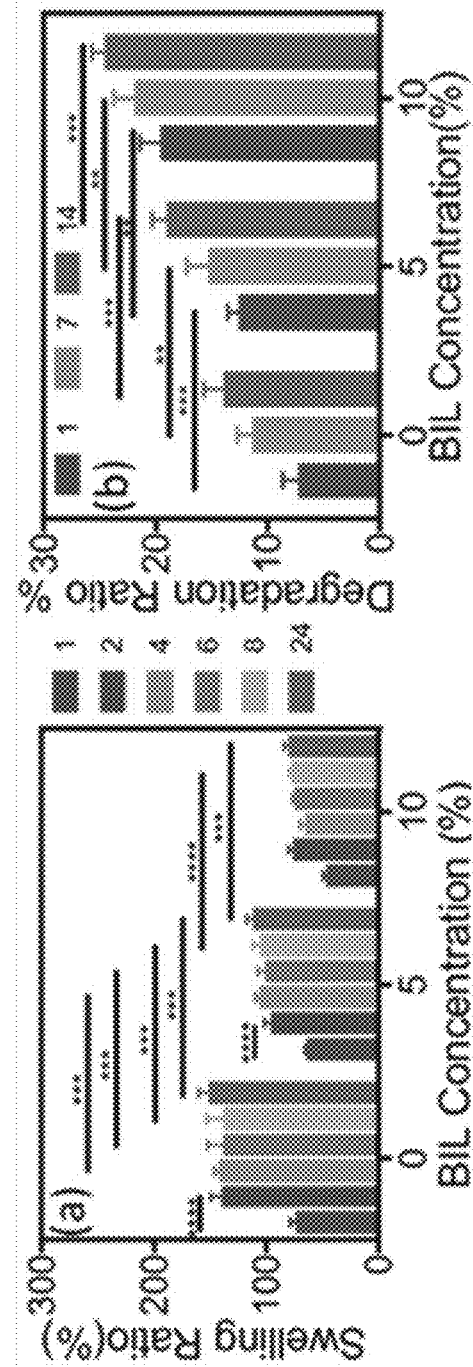
FIGS. 3A-3B are graphs showing results of swelling and degradation studies of GelMA/BIL.

The present invention relates to novel biocompatible oxygen gas generating devices that can be implanted into a living subject. In certain embodiments, the oxygen gas generating devices can be used to deliver oxygen gas to tissue in a subject, thereby stimulating tissue growth and repair. In other embodiments, the devices operate by electrolytically splitting endogenous water in a subject. In yet other embodiments, the device further includes an implantable supercapacitor capable of supplying energy to the oxygen gas generating device.

Oxygen Gas Generating Electrochemical Cell

In one aspect, the invention provides a biocompatible oxygen gas generating electrochemical cell. In certain embodiments, the oxygen gas generating electrochemical cell includes a biocompatible conductive hydrogel electrolyte, a biocompatible anode, and a biocompatible cathode.

In certain embodiments, the biocompatible conductive hydrogel electrolyte can be an electrically conductive hydrogel that includes a biopolymer backbone and at least one ionic liquid side chain conjugated to the biopolymer backbone.

In certain embodiments, the biopolymer backbone includes at least one biopolymer selected from the group consisting of gelatin, gelatin methacrylate, elastin, hyaluronic acid (HA), alginate, polyethylene glycol (PEG), 2-hydroxyethyl methacrylate (HeMA), and poly glycerol sebacate (PGS). In other embodiments, the biopolymer backbone includes gelatin methacrylate (GelMa).

In certain embodiments, the hydrogel electrolyte can be about 10% to about 20% (w/v) of the biopolymer backbone. The hydrogel electrolyte can be, in some embodiments, about 10, 11, 12, 13, 14, 15, 16, 17, 18, 19, or 20% (w/v) of the biopolymer backbone.

In certain embodiments, the at least one ionic liquid side chain is at least one selected from the group consisting of choline acrylate, choline acetate, choline itaconate, and choline salicylate. In other embodiments, the at least one ionic liquid side chain is choline acrylate. In certain embodiments, the hydrogel electrolyte can be about 1% to about 20% (w/v) of the at least one ionic liquid side chain. In some embodiments, the hydrogel electrolyte can be about 1, 2, 3, 4, 5, 6, 7, 8, 9, 10, 11, 12, 13, 14, 15, 16, 17, 18, 19, or about 20% (w/v) of the at least one ionic liquid side chain.

In certain embodiments, the biocompatible conductive hydrogel electrolyte can include a polymer containing at least one monomeric unit of formula (n=1-1,000)

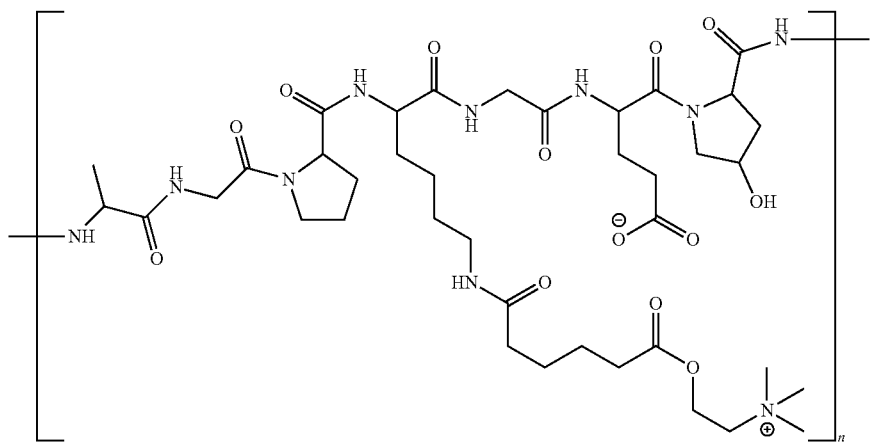

In certain embodiments, the biocompatible conductive hydrogel electrolyte further includes at least one photoinitiator used to form the hydrogel. In other embodiments, the at least one photoinitiator is reactive upon exposure to light in the IR (700-1,000,000 nm), visible (400-700 nm) and/or UV (10-400 nm) range. In other embodiments, the at least one photoinitiator is selected from the group consisting of lithium phenyl-2,4,6-trimethylbenzoyl phosphinate (LAP), eosin Y, 2-Hydroxy-2-methylpropiophenone, 2-Methyl-4'-(methylthio)-2-morpholinopropiophenone, and 2-Hydroxy-4'-(2-hydroxyethoxy)-2-methylpropiophenone (Irgacure).

In certain embodiments, the biocompatible conductive hydrogel electrolyte further includes at least one type of biological cell or cells. In one embodiment, the biological cells are selected from a group consisting of cardiomyocytes (CMs), cardiac fibroblasts(CFs), and mesenchymal stem cells (MSCs).

In certain embodiments, the biocompatible conductive hydrogel electrolyte is patterned into a specific conformation. In other embodiments, the biocompatible conductive hydrogel electrolyte is formed into a grid-like pattern. In yet other embodiments, the biocompatible conductive hydrogel electrolyte is 3D printed. In a non-limiting example, the biocompatible conductive hydrogel electrolyte that includes biological cells is 3D printed as reticular networks of up to five layers (1 mm in total thickness).

In certain embodiments, the biocompatible anode and biocompatible cathode each independently include at least one material selected from the group consisting of graphene hydrogel, cobalt, zinc, silicon nanoparticles, graphene oxide, magnesium, iron, cobalt phosphate, nickel, nickel phosphate, combination of nickel and phosphate, and combination of nickel phosphate and cobalt phosphate. In other embodiments, the biocompatible anode and biocompatible cathode each include cobalt phosphate, graphene hydrogel, and optionally silicon nanoparticles. In yet other embodiments, the biocompatible anode and biocompatible cathode each independently include about 1% to about 5% cobalt phosphate (w/v). In yet other embodiments, the silicon nanoparticles are laponite particles.

Figure 8A:
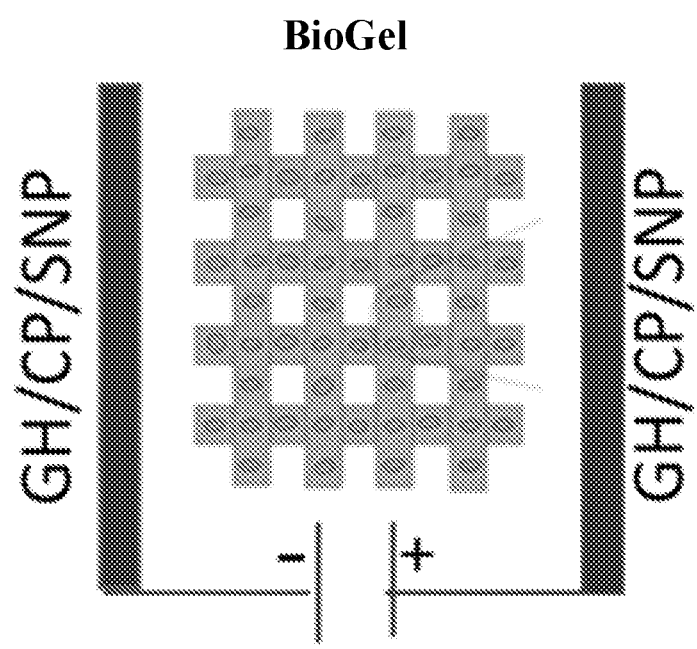
FIG. 8A is a schematic of a self-oxygen gas generating biomaterial/electrochemical cell of the invention.

In certain embodiments, the biocompatible oxygen gas generating electrochemical cell is assembled according to FIG. 8A, wherein the biocompatible conductive hydrogel electrolyte (BioGel) is present between the biocompatible anode and the biocompatible cathode.

In certain embodiments, the biocompatible anode and the biocompatible cathode are 3D printed.

Power Source/Supercapacitor Devices

The invention further provides a biocompatible supercapacitor device. In certain embodiments, the biocompatible supercapacitor device includes a biocompatible conductive hydrogel electrolyte, and a plurality of electrodes.

In certain embodiments, the biocompatible conductive hydrogel electrolyte is an electrically conductive hydrogel that includes a biopolymer backbone and at least one ionic liquid side chain conjugated to the biopolymer backbone.

In certain embodiments, the biopolymer backbone includes at least one biopolymer selected from the group consisting of gelatin, gelatin methacrylate, elastin, hyaluronic acid (HA), alginate, polyethylene glycol (PEG), 2-hydroxyethyl methacrylate (HeMA), and poly glycerol sebacate (PGS), and mixtures thereof. In other embodiments, the biopolymer backbone can be gelatin methacrylate (GelMa).

In certain embodiments, the ionic liquid side chain includes choline. In yet other embodiments, in the ionic liquid side chain the choline is conjugated with an acrylate or methacrylate group, which forms a covalent group to a methacrylate or acrylate group in the biopolymer backbone. In yet other embodiments, the ionic liquid side chain includes choline acrylate or choline methacrylate.

In certain embodiments, the at least one ionic liquid side chain is at least one selected from the group consisting of choline acrylate, choline acetate, choline itaconate, and choline salicylate. In other embodiments, the at least one ionic liquid side chain is choline acrylate. In certain embodiments, the biocompatible conductive hydrogel electrolyte includes about 1% to about 20% (w/v) of the at least one ionic liquid side chain. In some embodiments, the biocompatible conductive hydrogel electrolyte can be about 1, 2, 3, 4, 5, 6, 7, 8, 9, 10, 11, 12, 13, 14, 15, 16, 17, 18, 19, or about 20% (w/v) of the at least one ionic liquid side chain.

In certain, non-limiting embodiments of the invention, the biocompatible conductive hydrogel electrolyte can include a polymer containing at least one monomeric unit of formula (n=1-1,000).

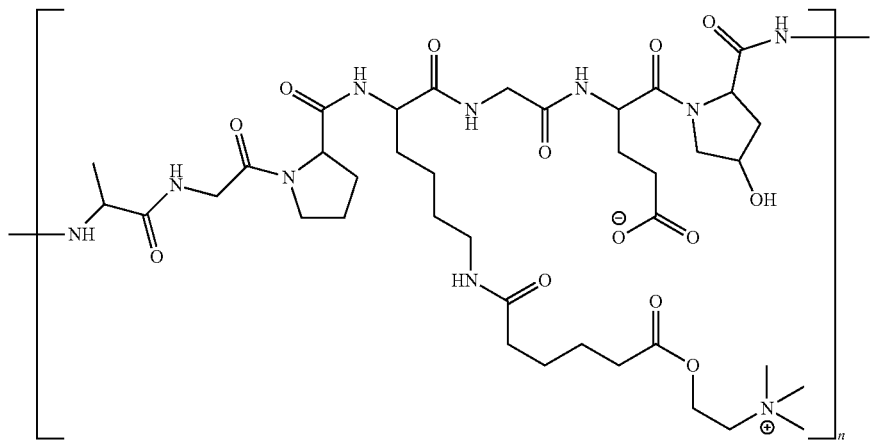

In certain embodiments, the biocompatible conductive hydrogel electrolyte further includes at least one photoinitiator used to form the hydrogel. In other embodiments, the at least one photoinitiator is reactive upon exposure to light in the IR (700-1,000,000 nm), visible (400-700 nm), and/or UV (10-400 nm) range. In other embodiments, the at least one photoinitiator is selected from the group consisting of lithium phenyl-2,4,6-trimethylbenzoyl phosphinate (LAP), eosin Y, 2-Hydroxy-2-methylpropiophenone, 2-Methyl-4'-(methylthio)-2-morpholinopropiophenone, and 2-Hydroxy-4'-(2-hydroxyethoxy)-2-methylpropiophenone (Irgacure).

In certain embodiments, the biocompatible conductive hydrogel electrolyte is 3D printed.

In certain embodiments, the plurality of biocompatible electrodes comprise at least one material selected from the group consisting of graphene hydrogel, silicon nanoparticles, graphene oxide, cobalt, cobalt phosphate, zinc, magnesium, iron, nickel, nickel phosphate, combination of nickel and phosphate, and combination of nickel phosphate and cobalt phosphate. In other embodiments, the biocompatible electrodes comprise graphene hydrogel and silicon nanoparticles. In yet other embodiments, the biocompatible electrodes comprise about 1% to about 10% (w/v) silicon nanoparticles. In yet other embodiments, the silicon nanoparticles are laponite particles.

Figure 8B:
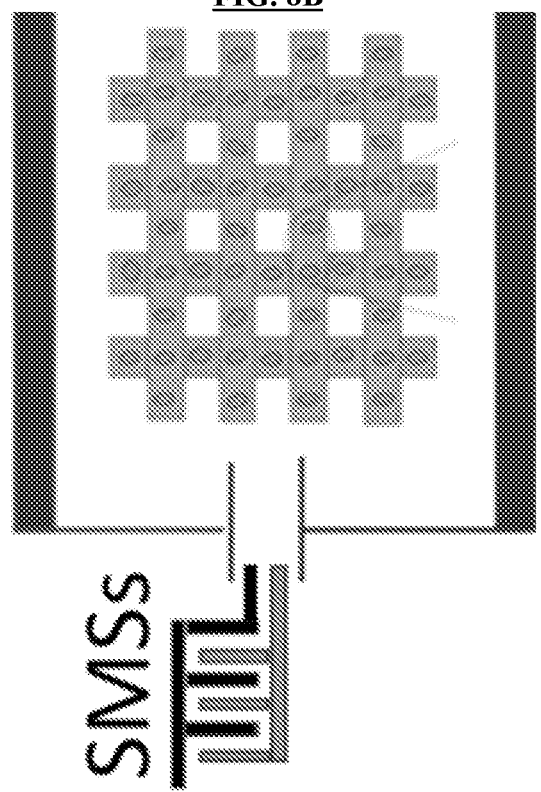
FIG. 8B is a schematic of an implantable oxygen gas generating tissue scaffold device of the invention.
Figures 11A, 11B, 11C, 11D, 11E, 11F:
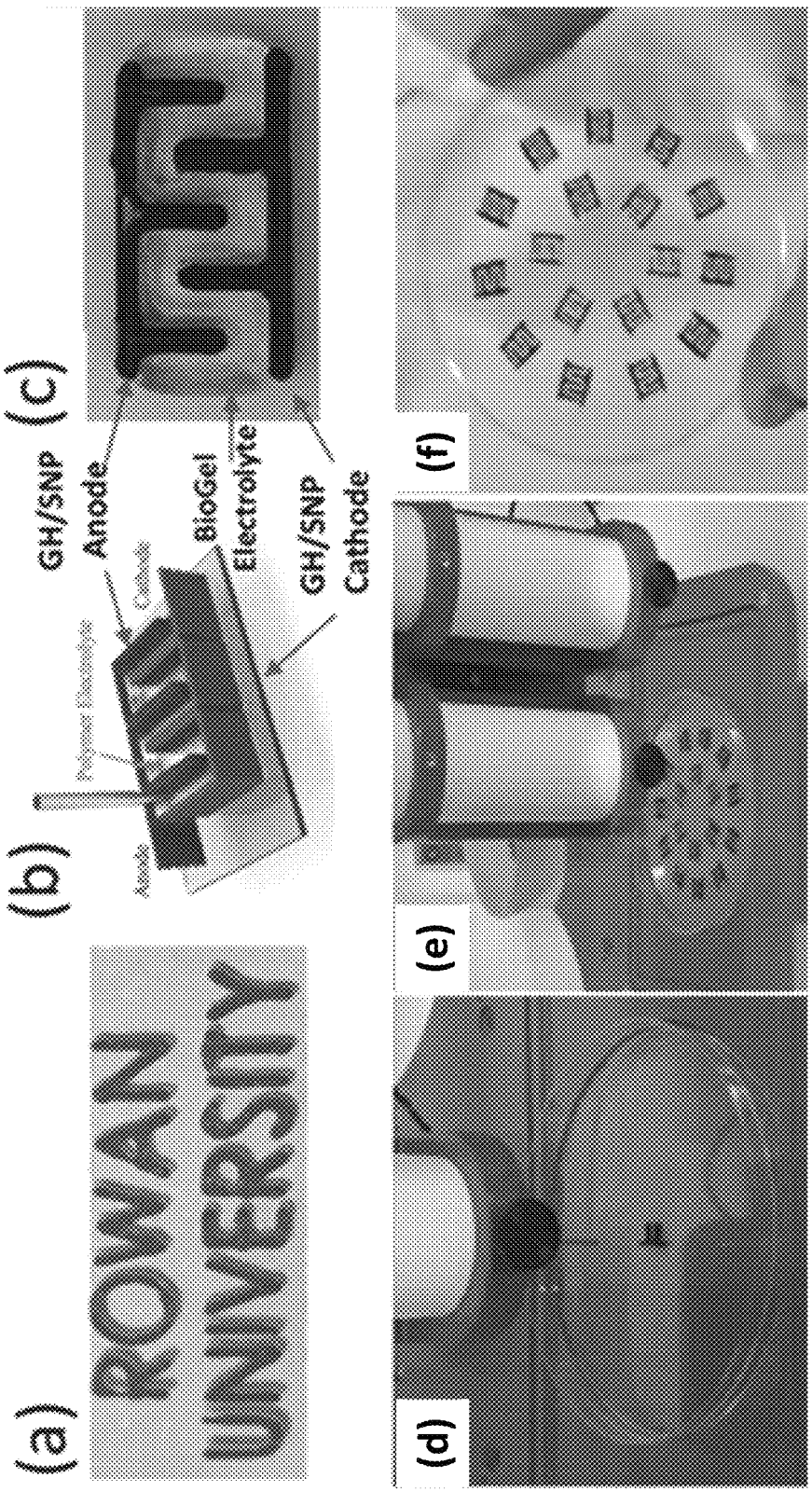
FIGS. 11A-11F are images of oxygen gas generating devices of the invention.

In certain embodiments, the biocompatible supercapacitor device is assembled according to FIG. 8B, FIG. 11B or FIG. 11C, wherein the biocompatible conductive hydrogel electrolyte (BioGel) is present between the biocompatible electrodes. Referring now to FIG. 11C, in certain embodiments, the biocompatible electrodes are shaped such that they form an interlocking comb-like structure. In other embodiments, the biocompatible electrodes are shaped such that the surface area contact with the biocompatible conductive hydrogel electrolyte is maximized.

In certain embodiments, the biocompatible supercapacitor device has a power density of about 5 to about 20 W/g. In other embodiments, biocompatible supercapacitor device has a power density above about 50 W/g. In yet other embodiments, biocompatible supercapacitor device has a specific capacitance of about 100 F/g to about 300 F/g.

In certain embodiments, the biocompatible electrodes are 3D printed.

In one embodiment, the biocompatible supercapacitor device can operate at about a neutral pH. The biocompatible supercapacitor device can operate at, in some embodiments, a pH of about 6 to about 7, or about 7 to about 8, or of about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or about 8.0. In some embodiments, the biocompatible supercapacitor device can operate at a human physiological pH (about pH 7.4).

Oxygen-Generating Implantable Devices & Methods

In yet another aspect, the invention provides an oxygen generating implantable device includes at least one biocompatible supercapacitor device of the invention and at least one electrochemical cell of the invention. In certain embodiments, the at least one biocompatible supercapacitor device and the at least one electrochemical cell are in electronic communication. In other embodiments, the at least one biocompatible supercapacitor device and the at least one electrochemical cell are in electronic communication, as shown in FIG. 8B. In yet other embodiments, the at least one biocompatible supercapacitor device and the at least one electrochemical cell are in electronic communication, such that the biocompatible supercapacitor device is capable of providing electrical energy to the at least one electrochemical cell.

In certain embodiments, the implantable device is implanted into a subject subcutaneously, thereby providing a means for supplying oxygen gas ($O_2$) to a tissue within the subject. In other embodiments, the implantable device electrolytically splits water ($H_2O$) in order to produce oxygen gas ($O_2$). In yet other embodiments, the water is endogenous water contained within the tissue of the subject.

In certain embodiments, the implantable device produces about $0.05 \times 10^{-3}$ µmol/sec $O_2$ to about $10 \times 10^{-3}$ mmol/sec $O_2$. The implantable device, in some embodiments, can produce about $0.05 \times 10^{-3}$, $0.1 \times 10^{-3}$, $0.15 \times 10^{-3}$, $0.25 \times 10^{-3}$, $0.30 \times 10^{-3}$, $0.35 \times 10^{-3}$, $0.40$–$10^{-3}$, $0.45 \times 10^{-3}$, $0.50 \times 10^{-3}$, $0.55 \times 10^{-3}$, $0.60 \times 10^{-3}$, $0.65 \times 10^{-3}$, $0.70 \times 10^{-3}$, $0.75 \times 10^{-3}$, $0.80 \times 10^{-3}$, $0.85 \times 10^{-3}$, $0.90 \times 10^{-3}$, $0.95 \times 10^{-3}$, $1.0 \times 10^{-3}$, $1.5 \times 10^{-3}$, $2.0 \times 10^{-3}$, $2.5 \times 10^{-3}$, $3.0 \times 10^{-3}$, $3.5 \times 10^{-3}$, $4.0 \times 10^{-3}$, $4.5 \times 10^{-3}$, $5.0 \times 10^{-3}$, $5.5 \times 10^{-3}$, $6.0 \times 10^{-3}$, $6.5 \times 10^{-3}$, $7.0 \times 10^{-3}$, $7.5 \times 10^{-3}$, $8.0 \times 10^{-3}$, $8.5 \times 10^{-3}$, $9.0 \times 10^{-3}$, $9.5 \times 10^{-3}$, or about $10.0 \times 10^{-3}$ µmol/sec $O_2$.

In another embodiment, the invention provides a method of treating a tissue injury in a subject, the method comprising subcutaneously implanting an implantable device of the invention into the subject. In certain embodiments, the implantable device is implanted on, near, and/or in close proximity to the tissue injury.

In certain embodiments, the tissue injury is at least one selected from the group consisting of any ischemic reperfusion injuries, muscle injury, a pancreatic tissue injury, and a neural tissue injury. In certain embodiments, the injured tissue is a transplanted tissue. In other embodiments, the injured tissue is an implanted engineered tissue.

In certain embodiments, the method treats or prevents hypoxia (<5% oxygen gas) and/or anoxia (<0.5% oxygen gas) in the tissue of the subject. In other embodiments, the method treats or prevents tissue necrosis. In yet other embodiments, the method promotes angiogenesis in the injured tissue. In yet other embodiments, the method promotes aerobic respiration and the production of adenosine triphosphate in the injured tissue.

In one embodiment, the implantable device can operate at about a neutral pH. The implantable device can operate at, in some embodiments, a pH of about 6 to about 7, or about 7 to about 8, or of about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or about 8.0. In some embodiments, the implantable device can operate at a human physiological pH (about pH 7.4).

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in tissue engineering and biomaterial science are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

A "bio-ionic liquid" or "ionic liquid" as used herein refers to a salt that has a melting temperature below room temperature (e.g., the melting temperature is less than 10° C., less than 15° C., less than 20° C., less than 25° C., less than 30° C., or less than 35° C.) and that contains a cation and an anion, at least one of which is a biomolecule (i.e., a molecule found in a living organism) or a biocompatible organic molecule. Examples of bio-ionic liquids are organic salts of choline, such as carboxylate salts of choline, choline bicarbonate, choline maleate, choline succinate, and choline propionate. An ionic constituent of a bio-ionic liquid is a cation or anion component of a bio-ionic liquid. Examples of ionic constituents of bio-ionic liquids for use in the invention are biocompatible organic cations such as choline and other biocompatible quaternary organic amines, as well as biocompatible organic anions such as carboxylic acids, including formate, acetate, propionate, butyrate, malate, succinate, citrate, and the like.

A "biocompatible polymer" as used herein refers to an organic polymer found in a living organism or compatible with a living organism. The polymer can be naturally occurring or synthetic and charged or uncharged. The polymer is sufficiently hydrophilic to be capable of forming a hydrogel or serving as a component of a hydrogel. Examples of biocompatible polymers for use in the invention include gelatin, elastin, elastin like polypeptides (ELP), chitosan, tropoelastin, collagen, hyaluronic acid (HA), alginate, poly (glycerol sebacate) (PGS), poly(ethylene glycol) (PEG), and/or poly(lactic acid) (PLA). A biocompatible polymer, conjugate, or other molecule or composition is capable of being in contact with cells without compromising their viability, such as by causing cell death, inhibition of cell proliferation, or exhibiting toxic effects on cellular metabolism or physiology of the organism. For example, a hydrogel is biocompatible if cells applied on its surface or embedded within its matrix remain viable as measured over a period of days, e.g., 5 days, 10 days, or 30 days.

As used herein, two elements (such as, but not limited to, an electrode and an electrolyte) are in "electrochemical contact" wherein they are at least in partial physical contact and an exchange of electrons and/or ions is possible between the two elements.

As used herein, the terms "functionalized", "covalently bound" or "covalently conjugated" refers to the formation of a covalent bond between two chemical species or moieties. Covalent bonds are to be taken to have the meaning commonly accepted in the art, referring to a chemical bond that involves the sharing of electron pairs between atoms.

As used herein, the term "gel" refers to a three-dimensional polymeric structure that itself is insoluble in a particular liquid but which is capable of absorbing and retaining large quantities of the liquid to form a stable, often soft and pliable, but always to one degree or another shape-retentive, structure. When the liquid is water, the gel is referred to as a hydrogel. Unless expressly stated otherwise, the term "gel" is used throughout this application to refer both to polymeric structures that have absorbed a liquid other than water and to polymeric structures that have absorbed water, it being readily apparent to those skilled in the art from the context whether the polymeric structure is simply a "gel" or a "hydrogel."

As used herein, "interdigitate" electrodes refers to electrodes that have at least a section of two interlocking comb-shaped electrode arrays, similar to a zipper.

The terms "patient," "subject" or "individual" are used interchangeably herein, and refer to any animal, or cells thereof whether in vitro or in situ, amenable to the methods described herein. In a non-limiting embodiment, the patient, subject or individual is a human. In other embodiments, the subject is a non-human mammal including, for example, livestock and pets, such as ovine, bovine, porcine, canine, feline, primate and murine mammals.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein.

Such treatments may be specifically tailored or modified, based on knowledge obtained from the field of pharmacogenomics.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: BIL: bio-ionic liquid (more specifically, choline acrylate); DPBS: Dulbecco's phosphate buffered saline; DSC: Differential Scanning calorimetry; FTIR: Fourier transform infrared spectroscopy; GelMA: gelatin methacrylate; GelMA/BIL: choline acrylate functionalized gelatin methacrylate; GH: graphene hydrogel; GH/SNP: graphene hydrogel/silicon nanoparticles; GO: graphene oxide; GPC: Gel Permeation Chromatography; MA: methacrylic acid; ORBs: oxygen gas releasing biomaterials; ROS: reactive oxygen species; SNP: silicon nanoparticles; TEOA: triethanolamine; Tg: glass transition temperature.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. Although the description herein contains many embodiments, these should not be construed as limiting the scope of the invention but as merely providing illustrations of some of the presently preferred embodiments of the invention.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, with art-recognized alternatives and using no more than routine experimentation, are within the scope of the present application. In general the terms and phrases used herein have their art-recognized meaning, which can be found by reference to standard texts, journal references and contexts known to those skilled in the art. Any preceding definitions are provided to clarify their specific use in the context of the invention.

The following examples further illustrate aspects of the present invention. However, they are in no way a limitation of the teachings or disclosure of the present invention as set forth herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Materials and Methods

Synthesis of Choline Acrylate (BIL)

Choline bicarbonate (1 mol) or Choline bitartrate (1 mol) was mixed with acrylic acid (1 mol) and reacted at 50° C. for 5 hr. The remaining acrylic acid was extracted with methylene chloride ($CH_2Cl_2$) from the reaction mixture. The acrylated BIL was purified with rotary evaporation for 24 hr followed by freeze drying.

Synthesis of Gelatin Methacrylate

Type A porcine skin gelatin was mixed at 10% (w/v) into Dulbecco's phosphate buffered saline (DPBS; GIBCO) at 60° C. and stirred until fully dissolved. MA was added until the target volume was reached at a rate of 0.5 mL/min to the gelatin solution under stirred conditions at 50° C. and allowed to react for 1 h. The fraction of lysine groups reacted was modified by varying the amount of MA present in the initial reaction mixture. Following a 5× dilution with additional warm (40° C.) DPBS to stop the reaction, the mixture was dialyzed against distilled water using 12-14 kDa cutoff dialysis tubing for 1 week at 40° C. to remove salts and methacrylic acid. The solution was lyophilized for 1 week to generate a white porous foam and stored at −80° C. until further use.

Synthesis of GelMA/BIL

Acrylated BILs and GelMA were mixed in phosphate-buffered saline (PBS) in various ratios and concentrations and polymerized with visible light in the presence of a photo cross-linker (lithium phenyl-2,4,6 trimethylbenzoylphosphinate [LAP], Sigma Aldrich).

In Vitro Degradation Tests

Conjugated GelMA/BIL samples were freeze-dried, weighed and placed in 24-well plate with 1 ml of DPBS or DPBS supplemented with 10% FBS solutions at 37° C. in an oven continuously for 2 weeks. The DPBS/FBS solutions were refreshed every 3 days to maintain constant enzyme activity. At prearranged time points (after 1, 7 and 14 days), the DPBS/FBS solutions were removed and the samples were freeze-dried for 24 h and weighed.

Biocompatibility Procedures $2 \times 10^4$ cells/scaffold were seeded on the surface of the hydrogels and placed in 24-well plates with 500 μm of growth medium (DMEM supplemented with 10% fetal bovine serum 2D cultures were maintained at 37° C. in a 5% $CO_2$ humidified atmosphere, for 10 days and culture medium was replaced every 48 h. The viability of primary C2C12 grown on the surface of GelMA and GelMA/Bio-IL hydrogels was evaluated using a commercial live/dead viability kit (Invitrogen), according to instructions from the manufacturer. Briefly, cells were stained with 0.5 μl/ml of calcein AM and 2 μl/ml of ethidium homodimer-1 (EthD-1) in DPBS for 15 min at 37° C. Fluorescent image acquisition was carried out at days 1, 4, and 7 post-seeding using an AxioObserver Z1 inverted microscope (Zeiss). Viable cells appeared as green and apoptotic/dead cells appeared as red. The number of live and dead cells was quantified using the ImageJ software. Cell viability was determined as the number of live cells divided by the total number of live and dead cells using ImageJ.

The metabolic activity of the cells was evaluated at days 1, 4, 7 post-seeding, using a PrestoBlue assay (Life Technologies) according to instructions from the manufacturer. Briefly, 2D and 3D cultures of primary CMs were incubated in 400 μL of growth medium with 10% PrestoBlue reagent for 2 h at 37° C. The resulting fluorescence was measured (excitation 530 nm; emission 590 nm) using a SpectraMax. Control wells without cells were used to determine the background for all experiments.

Spreading on the surface of the engineered composite hydrogels was visualized through fluorescent staining of F-actin filaments and cell nuclei. Briefly, the protocol is: Prepare 0.1% PBT, fresh fix solution (4% PFA in 0.1% PBT), and staining solution (DAPI and phalloidin in PBS at a 1:1000 dilution); Remove media from cells and dispense 150 μl/well of 1× PBS, into each 12-well plate; Remove PBS by shake out method; Dispense 150 μl/well of fix solution and fix cells for 25 minutes, discard the fix solution by shake out method; Dispense 200 μl/well of PBT and incubate for 5 minutes, shake out and repeat two more times for a total of 3 washes; Remove PBT dispense 150 μl/well staining solution and incubate for 25-30 minutes; Discard the staining solution and dispense 150 μl/well of 1× PBS, allow to sit for 5 minutes, shake out and repeat two more times for a total of 3 washes; Remove PBS by shake out method and add 50 μl/well of 1× PBS to keep the cells hydrated while imaging. Fluorescent image acquisition was carried out using an Axio Observer Z1 inverted microscope.

Cobalt-Phosphate Synthesis

To synthesize the CoP electrode materials, cobalt nitrate $(Co(NO_3)_2)$ in an aqueous solution (1M, 3 mL) was added to Ammonium phosphate$(NH_4)_3PO_4$ (1 M, 3 mL) or Sodium Phospahte $(Na_3PO_4)$ (1M, 3 ml) with stirring. After stirring for 2 h at room temperature, the resulting mixture was transferred into a teflon-lined stainless autoclave and heated in an oven at 200° C. for 6 h. The resulting sediments were washed with deionized ethanol and de ionized water thrice and then dried at 60° C. for 12 h to obtain the CoP electrode material.

Graphene Hydrogel Synthesis

Initially graphene oxide was synthesized by improved Hummer's method, a 9:1 mixture of concentrated $H_2SO_4$/$H_3PO_4$ (360:40 mL) was added to a mixture of graphite flakes (3.0 g, 1 wt equivalent) and $KMnO_4$ (18.0 g, 6 wt equivalent), producing a slight exotherm to 35-40° C. The reaction was then heated to 50° C. and stirred for 12 h. The reaction was cooled to room temperature and poured onto ice (400 mL) with 30% $H_2O_2$ (3 mL). For workup, the mixture was sifted through a metal sieve and then filtered through polyester fiber, the filtrate was centrifuged (4000 rpm for 4 h), and the supernatant was decanted away. The remaining solid material was then washed in succession with 200 mL of water, 200 mL of 30% HCl, and 200 mL of ethanol (twice); for each wash, the mixture was sifted through the U.S. Standard testing sieve and then filtered through polyester fiber with the filtrate being centrifuged (4000 rpm for 4 h) and the supernatant decanted away. The material remaining after this extended, multiple-wash process was coagulated with 200 mL of ether, and the resulting suspension was filtered over a PTFE membrane with a 0.45 μm pore size. The solid obtained on the filter was vacuum-dried overnight at room temperature, obtaining graphene oxide. Further, 0.3 ml of 2M L-ascorbic acid was added into a 50 mL beaker containing 6 mL 4.0 mg/ml graphene oxide aqueous solution with vigorous magnetic stirring until completely dissolving. The mixture was sealed in a Teflon lined autoclave and maintained at 180 C for 2 hours, then cooled to room temperature and stored.

Graphene Hydrogel/CoP Electrode Synthesis

To synthesize the Graphene hydrogel/CoP electrode materials, cobalt nitrate $(Co(NO_3)_2)$ in an aqueous solution (1M, 3 mL) was added to Ammonium phosphate$(NH_4)_3PO_4$ (1 M, 3 mL) or Sodium Phospahte $(Na_3PO_4)$ (1M, 3 ml) with stirring. After stirring for 2 h at room temperature, the resulting mixture was transferred into a teflon-lined stainless autoclave and heated in an oven at 200° C. for 6 h. The resulting sediments were washed with deionized ethanol and de ionized water thrice and then dried at 60° C. for 12 h to obtain the CoP electrode material. The obtained CoP material at different percentages varying from 0-100% wt/wt is added to 0.3 ml of 2M L-ascorbic acid in a 50 mL beaker containing 6 mL 4.0 mg/ml graphene oxide aqueous solution with vigorous magnetic stirring until completely dissolving. The mixture was sealed in a Teflon lined autoclave and maintained at 180 C for 2 hours, then cooled to room temperature and stored.

Graphene Hydrogel/SNP Electrode Synthesis

For graphene hydrogel, 0.3 ml of 2M L-ascorbic acid was added into a 50 mL beaker containing 6 mL 4.0 mg/ml graphene oxide aqueous solution with vigorous magnetic stirring until completely dissolving. The mixture was sealed in a Teflon lined autoclave and maintained at 180 C for 2 hours, then cooled to room temperature and stored. For, silica nanoparticle LAPONITE was used, for the electrode synthesis varying percentages (3-10) % of graphene hydrogel was physical mixed with (3-10)% of LAPONITE and 1% Gelatin in deionized water.

Solid State Oxygen Gas Producing Device Fabrication

CoP synthesized by previously mentioned method is mixed with LAPONITE and Gelatin at varying percentages in deionized water. (3-10) wt/v % of CoP was physical mixed with (3-10) wt/v % of LAPONITE and 1% Gelatin in deionized water and casted as electrode. For electrolyte, methacrylated polymers and choline acrylate (BIL) was used. To form Bio Ionic polymer electrolyte, the (10-25) wt/v % prepolymer and (0-20) wt/v % BILs were added to distilled water at varying final polymer concentrations and polymer/BILs ratios, then mixed with 0.5% (w/v) hydroxy methylpropiophenone (HEMP) photo initiator. Hydrogels were then rapidly photo crosslinked in the presence of UV light at a wavelength of 375 nm for 120 s and 60 s for GelMA and PEGDA respectively Soft Miniaturized Supercapacitor Device Fabrication For electrode graphene hydrogel synthesized by previously mentioned method is used in varying percentages (3-10)% was physical mixed with (3-10)% of LAPONITE and 1% Gelatin in deionized water. For electrolyte, (10-25) wt/v % prepolymer and (0-20) wt/v % BILs were added to distilled water at varying final polymer concentrations and polymer/BILs ratios, then mixed with 0.5% (w/v) hydroxy methylpropiophenone (HEMP) photo initiator. Further, the 3D printed designs were created using a SOLIDWORKS and fabricated into miniature supercapacitor using extrusion based printing.

Device 3D Printing Methods

A STL file was developed in SOLIDWORKS to 3D print the supercapacitor. the approach utilizes 3D printing of an electrode and electrolyte simultaneously, the graphene hydrogel/SNP synthesized was printed layer-by-layer as usual in extruder 1 using a ALLEVI2 printer. After which the extruder 2 prints electrolyte in between the electrodes according to the STL file designed. Further, the printed device was polymerized (405 nm, 40 mW/cm$^2$, 30 s), which formed a miniature supercapacitor. Each layer was usually in the range of 100-200 μm but can be adjusted by adjusting the print speed or pressure.

Oxygen Gas Generation Methods

The electrocatalysis of cobalt phosphate for oxygen generation was performed using a three-electrode cell in 1.0 M PBS electrolyte. CoP electro-catalysts were taken as the working electrode, gold (Au) was used as the counter electrode and Ag/AgCl was the reference electrode. Cyclic voltammetry (CV) and Linear sweep voltammetry (LSV) curves were obtained by sweeping the potential from −0.05 to 0.75 V (vs. Ag/AgCl) with a sweep rate of 10 mV s$_{-1}$ and all measured potentials are converted to the RHE scale according to the Nernst equation. The electrochemically active surface area was measured using the cyclic voltammetry curve at a non-faradaic reaction potential window from 0 to 1.0 V vs. RHE. The standard stability test of efficient electro-catalysts was carried out using chronopotentiometry at a constant current density of 10 mA cm$^{-2}$ for 10 h. Electrochemical impedance spectra (EIS) were measured with a 500-mV amplitude in the frequency range from 100 mHz to 100 kHz.

Example 1: Synthesis and Characterization of GelMA/BIL Electrolyte

To synthesize GelMA/BIL, first, choline bitartrate was acrylated with acrylic acid. Then choline bitartrate and acrylic acid were mixed at a mole ratio of (1:1). The mixture was reacted at 50° C. for 5 hr. The remaining acrylic acid was extracted from the reaction mixture using methylene chloride. The acrylated BILs were purified with rotary evaporation for 24 hr. The acrylated BILs and GelMA were then mixed in phosphate-buffered saline (PBS) and polymerized with visible light in the presence of photo cross-linker to form 3D conductive hydrogels. The GelMA concentration 5-10 (% w/v) and BILs concentration 5-10 (% w/v) were varied to create hybrid conductive hydrogels having tunable properties. Lithium phenyl-2,4,6 trimethylbenzoylphosphinate (LAP, Sigma Aldrich) was used as the crosslinking system for visible light photo-polymerization. The physical and electrical properties of the engineered hydrogels can be tuned by changing the light exposure time (from 20 s-120 s) and the LAP concentration (from 0.1% -1% w/v). By varying GelMa concentration, BILs concentration, LAP concentration and light exposure time, various GelMA/BILs were made having different mechanical and electrical properties. An ideal GelMA/BIL soft tissue scaffold of the invention should have compressive modulus>30 kPa, swelling ratio less than 50%, degradation rate between 20-50% after 14 days and the ideal electrolyte should have a conductivity greater than 1×10$^{-3}$ S/cm.

Mechanical properties of the GelMA/BILs are determined based on unconfined compression and tensile tests. In vitro degradation and swelling of the fabricated hydrogels are determined using DPBS or DPBS supplemented with 10% FBS solutions at 37° C. The chemical structures and thermal properties of the hydrogels are characterized using Fourier Transform Infrared Spectroscopy (FTIR), $^1$H-NMR and Differential Scanning Calorimetry (DSC). Gel Permeation Chromatography (GPC) is used to measure the molecular weight of hydrogels. DSC is used to measure the glass transition temperature (Tg) of GelMA/BIL Hydrogels. Scanning Electron Microscopy (SEM) is used to evaluate the physical structure of hydrogel with various formulation.

Figures 4A, 4B, 4C:
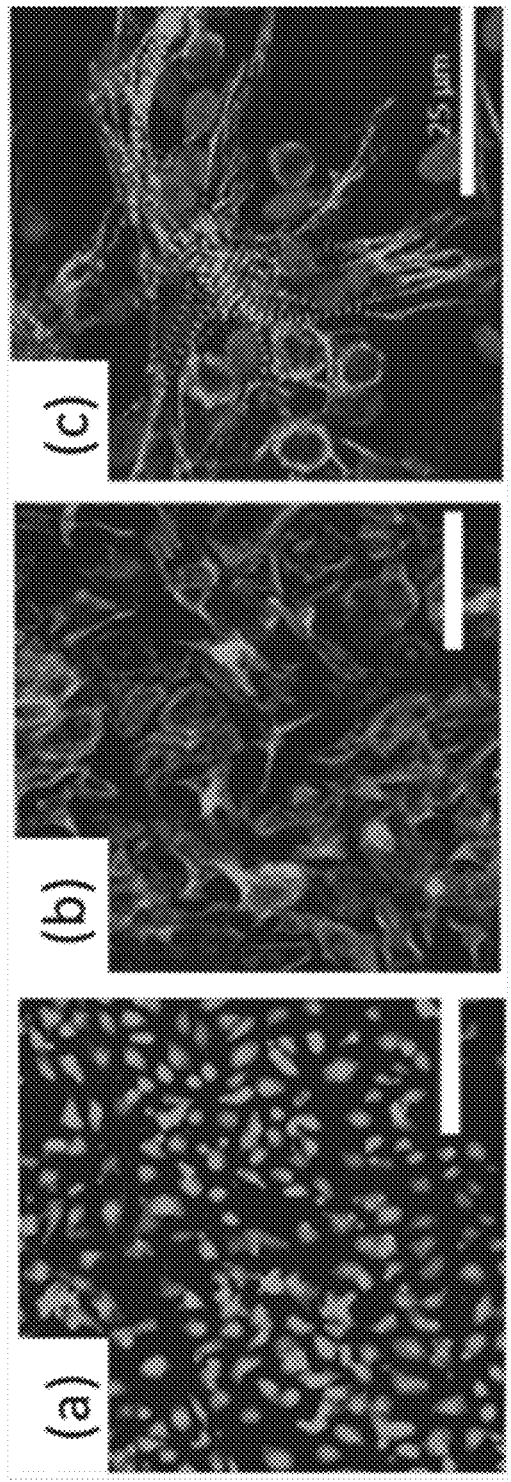
FIGS. 4A-4C are images showing in vitro 3D encapsulation of cardiomyocytes (CMs) and cardiac fibroblasts (CFs) in GelMA/BIL hydrogels.

In order to determine the biocompatibility of the engineered materials of the invention, the GelMA/BILs are contacted with mesenchymal stem cells (MSCs, Cellular Dynamics International). The cells are seeded on and into the engineered hydrogel at densities ranging from 1×10$^6$ cells/ml to 1×10$^8$ cells/ml. Cell viability and metabolic activities are determined on days 1, 4, 7, and 14. A GelMA/BIL formulation's biocompatibility has been determined with Cardiomyocyte Cells (CMs) cells. FIGS. 4A-4C show the cell viability and cell spreading of the GelMA/BIL using cardiomyocyte cells. The cell viability was performed with Live/Dead assay. The high percentage of live cells in the first 7 days suggests that the GelMA/BIL was cytocompatible. The Actin/DAPI assay was used for cell spreading. The density of cells (the number of cells per cm of hydrogel) increased between day 1 and day 7 of culture, demonstrating that the cells were proliferating.

Example 2: Device Fabrication and Oxygen Gas Production Kinetics

The GH/CoP electrodes were fabricated, and the electrochemical properties of the electrochemical cell were measured by a CH Instruments model 660 Electrochemical Station under a constant current discharging module using two-electrode configuration. Reactions and galvanostatic electrochemical impedance of electrodes were evaluated by a three electrode configuration, with Ag/AgCl as the reference electrode. The GH/CoP were used as electrodes, and GelMA/BIL was used as the electrolyte and a biocompatible solid-state oxygen gas producing device was fabricated.

Figures 5A, 5B, 5C:
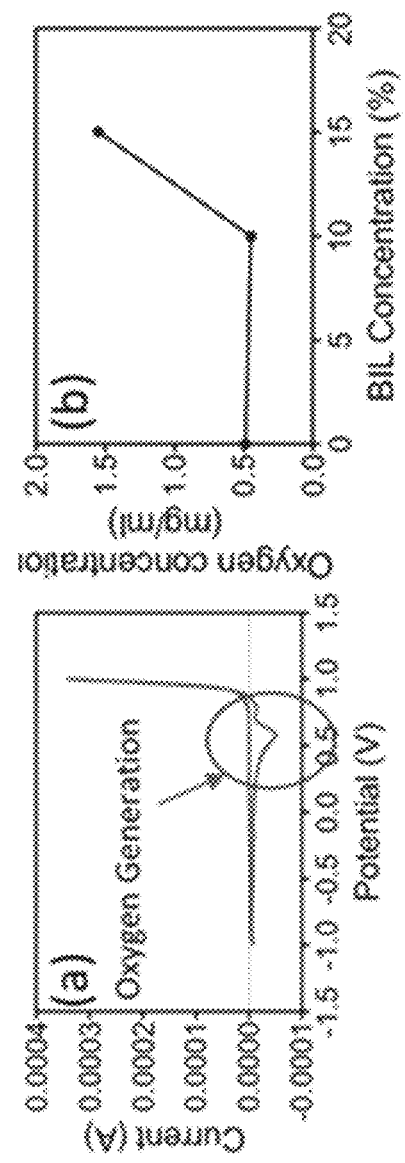
FIG. 5A is a cyclic voltammetry graph taken on an oxygenating tissue scaffold of the invention. The peak between 0.6-1.0 V shows successful production of oxygen gas. The generation of hydrogen gas was limited.
FIG. 5B is a graph showing changes in the oxygen gas generation rate by varying BILs concentration.
FIG. 5C is an image of an Actin/DAPI assay used to evaluate the cell spreading on an oxygenating tissue scaffold of the invention on day 3 after the cell culture.

The fabricated device was tested for oxygen gas generation (FIGS. 5A-5C). Initial cyclic voltammetry results showed successful production of oxygen gas inside the GelMA/BIL (FIG. 5A). The broad peak between 0.6 to 0.8 V indicated oxygen gas generation in the GH/CoP anode. An oxygen gas sensor (Ocean Optics, NeoFox System) was also used to measure the concentration of dissolved oxygen gas. The measured oxygen gas concentration by this method was 1.5 mg/L (FIG. 5B). Oxygen gas release kinetics were determined by using a ruthenium complex oxygen gas sensor (Ocean Optics, NeoFox System) under anoxic conditions (<0.1% $O_2$). Without intending to be limited to any particular theory, the concentration of GH/CoP in the electrode and the concentration of BILs in the GelMA/BIL directly correlate with oxygen gas generation rate.

For measurement of dissolved oxygen gas, the devices are placed into 12-well plates containing three mL of medium in each well and the plate is placed in a <0.1% $O_2$ incubator. The $H_2O_2$ concentration in the wells is assayed using an Amplex Red $H_2O_2$ detection kit (Sigma-Aldrich) by monitoring the absorbance at 555 nm using BIO13 Synergy plate reader. The concentration of $H_2O_2$ is quantified by comparing against a standard curve generated from $H_2O_2$ standards ranging from 0 to 40 μM. The leaching rates of various elements from the electrodes is measured with inductively coupled plasma mass spectrometry (ICP-MS) (Thermo Electron, X-Series ICP-MS with collision cell technology, CCT).

Mesenchymal stem cell viability was tested in the produced devices using an Actin/Dapi staining method (FIG. 5C). The high percentage of viable cells after three days indicate the cytocompatibility of the engineered self-oxygen gas releasing biomaterials.

Example 3: 3D Printing

Figure 6:
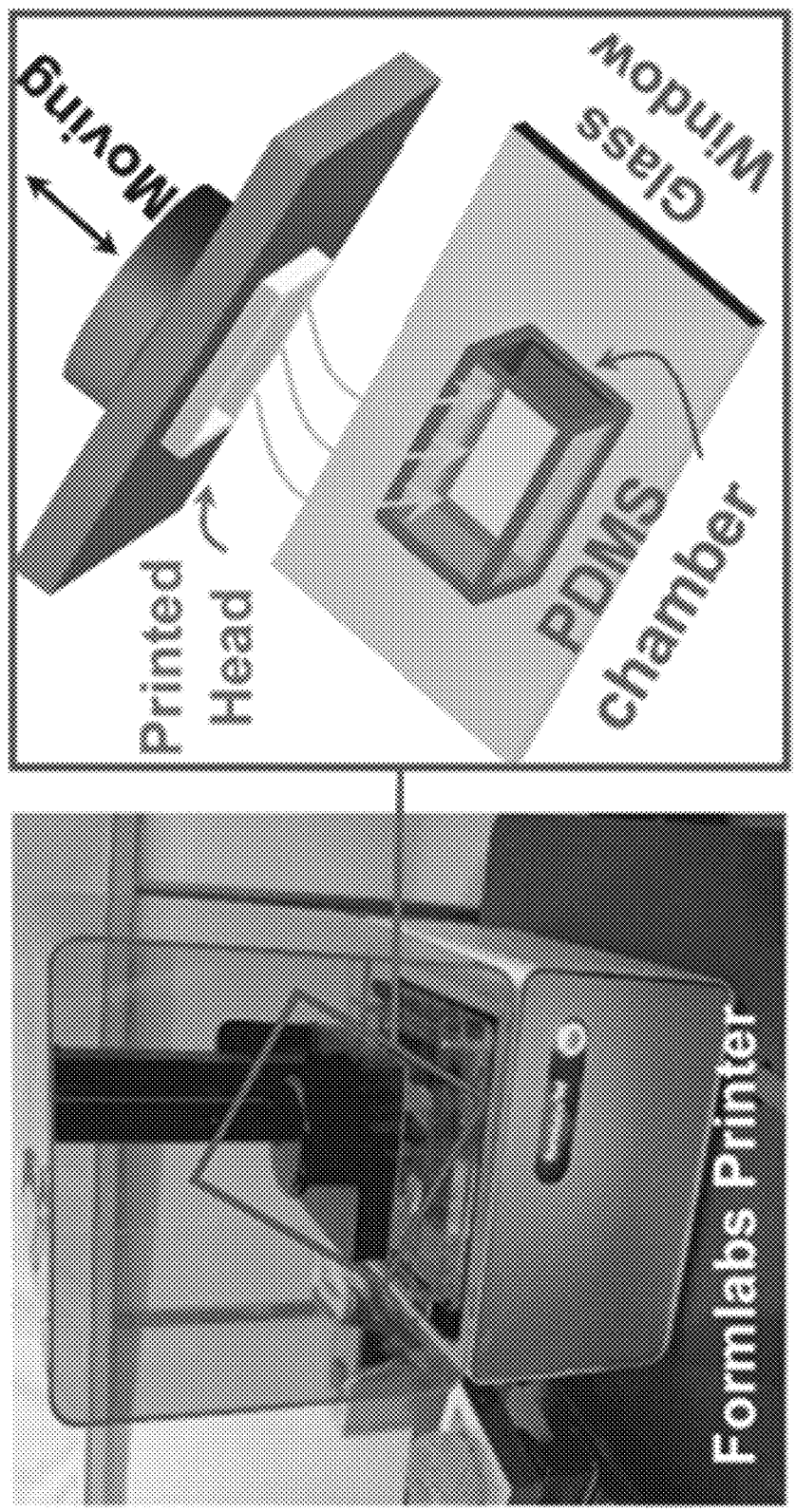
FIG. 6 is an image and a scheme showing a printer for fabricating a non-limiting device of the invention.
Figure 7:
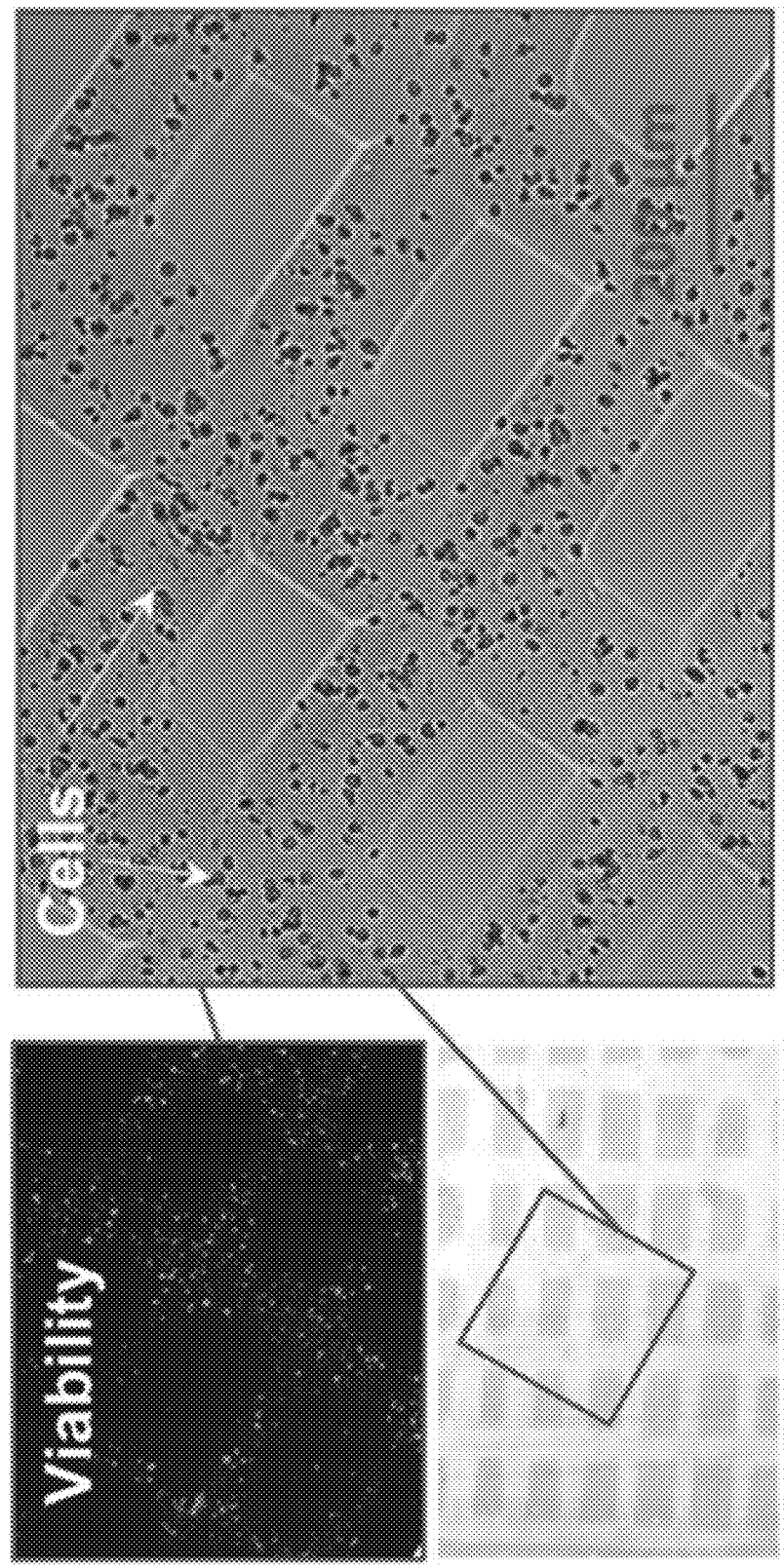
FIG. 7 is a set of images showing a reticular pattern of stem cell-laden GelMA/BIL (7%) bio printed by a home-built stereolithography (SLA; UV light) bioprinter and cell viability data at day 1 (Green: live cells).

A commercial SLA system was used to fabricate GelMA/BIL constructs as demonstrated in FIGS. 6A-6B. Fabrication parameters such as timing and thickness of GelMA/BIL can be altered and optimized to fit a number of desired parameters. Thin bioprinted cell-laden constructs were used as the building blocks following the process shown in FIGS. 7A-7C. Reticular networks up to five layers (1 mm in total thickness) were bioprinted using the GelMA/BIL and a MSC laden solution. Initial results shown in FIGS. 7A-7C showed good MSCs viability over a time frame of one week.

Fabrication of GelMA/BIL constructs can be scaled up using a commercial extrusion printer to print the electrochemical cell electrodes to make the printed solid state oxygen gas producing devices of the invention (FIGS. 8A-8B). To print GH/CoP electrodes, 3-5% (w/v) GH/CoP is mixed with 2-4% (w/v) Laponite and extruded with a 10 ml syringe. Laponite is used to help with the printability of GH/CoP electrode. The electrochemical properties and oxygen gas release kinetics will be determined as described Example 2. The $H_2O_2$ concentration is assayed using an Amplex Red $H_2O_2$ detection kit (Sigma-Aldrich) by monitoring the absorbance at 555 nm using a BIO13 Synergy plate-reader. The cytotoxicity of the 3D printed solid-state electrochemical cell for oxygen gas generation can be assessed using the same procedures as discussed elsewhere herein, or using any methods known in the art. The Live/Dead, Actin/DAPI, MTS assay and immunohistology can all be used to evaluate the cytotoxicity, metabolic activity and expression of MSCs markers.

Example 4: Soft Micro-Supercapacitors

In order to power the solid state oxygen gas producing devices of the invention, implantable solid state supercapacitors were developed, using the GelMA/BIL materials of the invention.

Figures 9A, 9B, 9C, 9D:
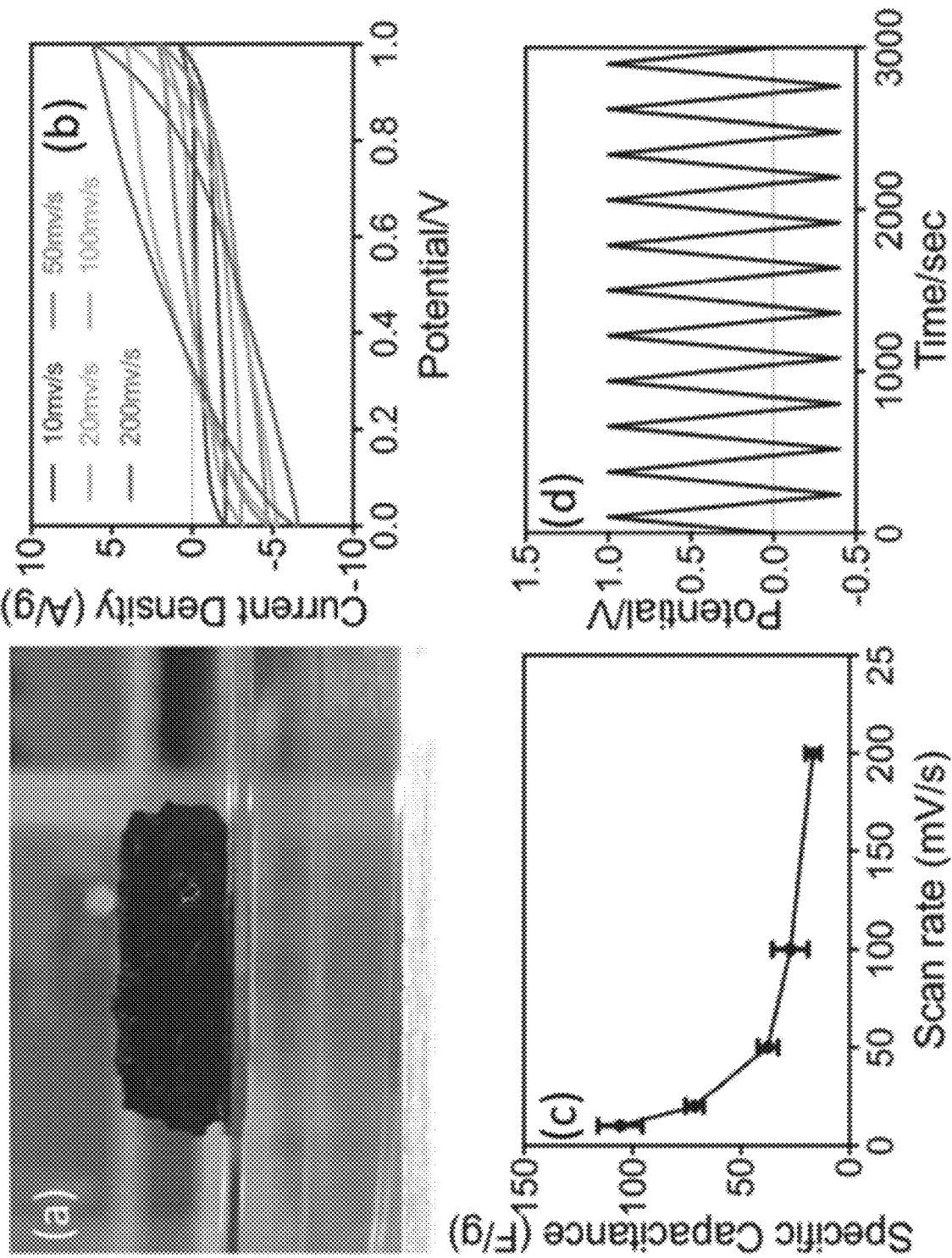
FIGS. 9A-9D are an image and graphs showing the electrochemical properties of graphene hydrogel (GH) electrodes.

Graphene hydrogel (GH)/silica nanoparticle (SNP) nanocomposites were fabricated and used as biocompatible soft hydrogel electrodes for supercapacitor fabrication. Graphene materials have been shown to be desirable supercapacitor electrodes with very good specific capacitances (160-240 F/g) as well as high rate capability and cycling stability. The electrodes' electrochemical properties were measured in a supercapacitor construct using PBS as the electrolyte. FIG. 9A shows a graphene hydrogel as synthesized. FIG. 9B shows a cyclic voltammetry graph of the GH hydrogel at various scan rates and FIG. 9C shows the specific capacitance of the fabricated GH hydrogel. A maximum specific capacitance of 98 F/g was obtained at a scan rate of 2 (mV/s). FIG. 9D shows the stability of the GH hydrogel capacitance with PBS as electrolyte up to 3000 time/sec cycles.

The graphene hydrogel materials were further modified by inclusion of graphene oxide (GO) and/or SNP (laponite) in order to modify the physical and electrochemical properties of the electrode. In one embodiment, GO was synthesized from graphite powder based on the modified Hummer's method. A 6 mL GO aqueous dispersion (10-40 mg/mL) was added to a 0.3 mL of 2M ascorbic acid aqueous solution, and the mixture was sealed in a Teflon-lined autoclave and maintained at 180° C. for 2 h. The autoclave was naturally cooled to room temperature, and the as-prepared GH was stored for further use. GH/SNP nanocomposite bio-ink was prepared by mixing GH hydrogels with varying concentrations of SNP (1-10% w/v). The as-prepared GH/SNP mixture was added to an agate capsule containing agate balls of 5 mm in diameter. The container was then fixed in a planetary ballmill machine and agitated at 500 rpm for 30 min. After ball milling and dispersion in a water mixture upon ultrasonic treatment, homogeneous GH/SNP inks were obtained and were suitable for 3D printing purposes.

Desired nanocomposite electrodes should have a specific capacitance of more than 100 F/g and power density more than 50 (w/g).

Example 5: 3D Printing of Soft Supercapacitors

An Allevi 2 bioprinting system adapted for an extrusion pressure range of 0-140 psi, with violet light (405 nm) irradiation capability was used to print the soft miniaturized supercapacitors (SMSs) of the invention. Visible light was used to crosslink the printed GelMA/BIL electrolyte. The GH/SNP electrode inks were stored in a cartridge of a 10 mL syringe fitted with a 32 gauge blunt-tipped nozzle (Jensen Global, Santa Barbara, Calif., USA), and the GelMA/BIL electrolytes were stored in a second syringe. Computer models for the constructs were designed using Creo Parametric 3.0 and imported into Repetier-Host software, where printing speed was set prior to extrusion. Hydrogel lines were extruded at printing pressures ranging from 60-130 psi and travel feed rates from 4-12 mm/s, under constant irradiation from the violet light source. Blunt needles of varying size (14 G-27 G) were used to extrude the hydrogels. FIGS. 11A-11F show 3D printed SMSs according to an embodiment of the invention.

Figures 10A, 10B:
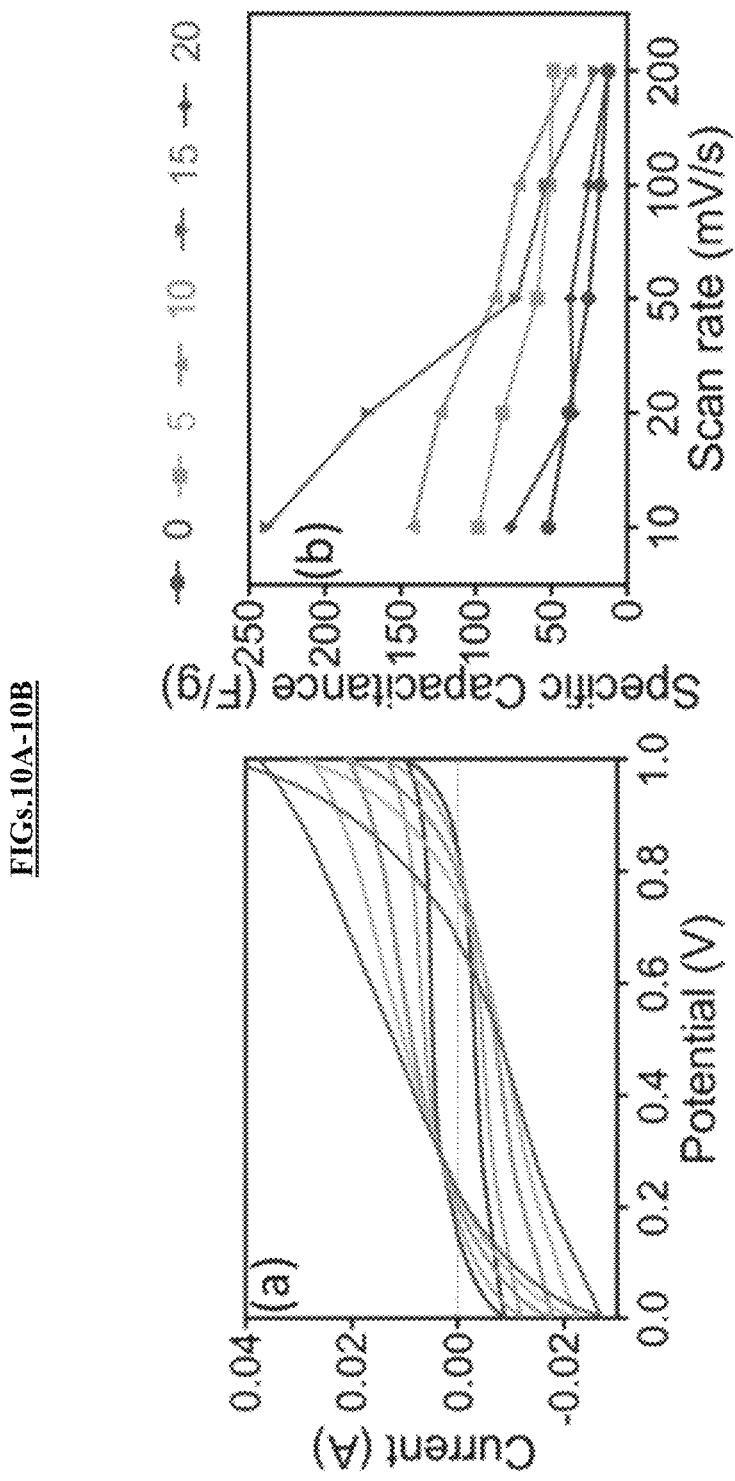
FIGS. 10A-10B are a CV (FIG. 10A) and specific capacitance graph (FIG. 10B) of a solid-state supercapacitor comprising a GH/SNP film electrode and a GelMA/BIL electrolyte indicating the effect of scan rate and BILs concentration on specific capacitance of SMSs.

The fabricated SMSs using GH/SNP as the electrode and GelMA/BIL as the electrolyte were then tested for capacitance. FIGS. 10A-10B show the CV curve and specific capacitance curve of the fabricated SMSs. In general, it was observed that with increasing scan rate, local electrolyte diffusion towards the electrode became difficult. This, in effect, decreased the interaction between the electrolyte and electrode thereby causing the specific capacitance to decrease. At lower scan rates, electrolyte ions have sufficient time to diffuse towards and interact with the electrode material, while higher scan rates encourage only surface accumulation. This trend was reflected for the compositions having 0 (% w/v) BILs to 10 (% w/v) BIL, the only difference being the concentration of diffusible ionic species brought about by the BILs functionalization via the polarization of the hydration spheres. An anomaly was seen with the further increase in the BILs loading to 15 and 20 (% w/v). At 15 (% w/v) BILs loading the specific capacitance jumped up in accordance with the trend, but dropped to a lower level with a further increase in loading to 20 (% w/v). Without intending to be limited to any particular theory, increased BILs loading also led to an increased propensity for network formation, as is seen in the swelling and degradation ratio experiments. With an increase in network formation, the natural diffusivity of ionic species decreased, leading to the observed decrease in specific capacitance even with increased ionic functionalization.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Embodiment 1 provides an implantable oxygen generating device comprising:
a. an oxygen generating, biocompatible electrochemical cell, wherein the electrochemical cell comprises a biocompatible cathode, a biocompatible anode, and a biocompatible hydrogel electrolyte, and wherein the hydrogel electrolyte is in electrochemical contact with the anode and the cathode of the cell;
b. a biocompatible power source, wherein the power source is a supercapacitor comprising a plurality of biocompatible electrodes and a biocompatible hydrogel electrolyte, and wherein the hydrogel electrolyte is in electrochemical contact with each of the plurality of the biocompatible electrodes of the power source;
wherein the biocompatible hydrogel electrolyte in the cell and the biocompatible hydrogel electrolyte in the power source are independently an electrically conductive hydrogel comprising a biopolymer backbone to which an ionic liquid side chain is conjugated; and
wherein the electrochemical cell is in electronic communication with the power source.

Embodiment 2 provides the device of embodiment 1, wherein the biopolymer backbone comprises a biopolymer selected from the group consisting of gelatin, gelatin methacrylate, elastin, hyaluronic acid (HA), alginate, polyethylene glycol (PEG), 2-hydroxyethyl methacrylate (HeMA), poly(ethylene glycol) diacrylate (PEGDA), and poly glycerol sebacate (PGS).

Embodiment 3 provides the device of any one of embodiments 1-2, wherein the hydrogel electrolyte comprises about 10% to about 20% (w/v) of the biopolymer backbone.

Embodiment 4 provides the device of any one of embodiments 1-3, wherein the ionic liquid side chain comprises choline.

Embodiment 5 provides the device of any one of embodiments 1-4, wherein at least one ionic liquid side chain is selected from the group consisting of choline acrylate, choline acetate, choline itaconate, choline salicylate, and any mixtures thereof.

Embodiment 6 provides the device of any one of embodiments 1-5, wherein the hydrogel electrolyte comprises about 0.1% to about 20% (w/v) of at least one ionic liquid side chain.

Embodiment 7 provides the device of any one of embodiments 1-6, wherein the hydrogel electrolyte further comprises a photoinitiator selected from the group consisting of lithium phenyl-2,4,6 trimethylbenzoylphosphinate (LAP), eosin Y, 2-Hydroxy-2-methylpropiophenone, 2-Methyl-4'-(methylthio)-2-morpholinopropiophenone, and 2-Hydroxy-4'-(2-hydroxyethoxy)-2-methylpropiophenone (Irgacure).

Embodiment 8 provides the device of any one of embodiments 1-7, wherein the hydrogel electrolyte comprises about 0.1% to about 1% (w/v) of at least one photoinitiator.

Embodiment 9 provides the device of any one of embodiments 1-8, wherein the hydrogel electrolyte in the electrochemical cell further comprises a biological cell.

Embodiment 10 provides the device of any one of embodiments 1-9, wherein the biological cell is selected from the group consisting of mesenchymal stem cell (MSC), cardiomyocyte, and cardiac fibroblast.

Embodiment 11 provides the device of any one of embodiments 1-10, wherein the electrochemical cell comprises reticular networks of the hydrogel electrolyte.

Embodiment 12 provides the device of any one of embodiments 1-11, wherein the reticular networks form a grid-like pattern.

Embodiment 13 provides the device of any one of embodiments 1-12, wherein the biocompatible anode and the biocompatible cathode each independently comprise at least one material selected from the group consisting of graphene hydrogel, cobalt, zinc, silicon nanoparticles, graphene oxide, magnesium, iron, cobalt phosphate, nickel, nickel phosphate, a combination of nickel and phosphate, and a combination of nickel phosphate and cobalt phosphate.

Embodiment 14 provides the device of any one of embodiments 1-13, wherein the biocompatible anode and biocompatible cathode each comprise cobalt phosphate, graphene hydrogel, and optionally silica nanoparticle/laponite.

Embodiment 15 provides the device of any one of embodiments 1-14, wherein the plurality of electrodes comprises graphene hydrogel.

Embodiment 16 provides the device of any one of embodiments 1-15, wherein the plurality of electrodes further comprises silica nanoparticles/laponite.

Embodiment 17 provides the device of any one of embodiments 1-16, wherein the biocompatible anode and biocompatible cathode each independently comprise about 1% to about 5% (w/v) of cobalt phosphate.

Embodiment 18 provides the device of any one of embodiments 1-17, wherein the device is biodegradable.

Embodiment 19 provides the device of any one of embodiments 1-18, wherein the device is biocompatible.

Embodiment 20 provides the device of any one of embodiments 1-19, wherein the electrochemical cell and the power source are 3D-printed.

Embodiment 21 provides the device of any one of embodiments 1-20, wherein the power source comprises an interdigitated structure comprising the hydrogel electrolyte and the plurality of biocompatible electrodes.

Embodiment 22 provides the device of any one of embodiments 1-21, wherein the device is operational at about neutral pH.

Embodiment 23 provides method of treating a tissue injury in a subject, the method comprising:
subcutaneously implanting the device of any one of embodiments 1-22 into the subject, wherein the device is implanted on, near, or in close proximity to the tissue injury.

Embodiment 24 provides the method of embodiment 23, wherein the tissue injury is at least one selected from the group consisting of an ischemic reperfusion injury, muscle injury, pancreatic tissue injury, and neural tissue injury.

Embodiment 25 provides an oxygen generating biocompatible device comprising
a. a biocompatible electrochemical cell comprising a graphene hydrogel/cobalt-phosphorous (GH/Co—P) alloy cathode, a graphene hydrogel/cobalt phosphate (GH/CoP$_i$) anode, and a biocompatible, conductive hydrogel electrolyte, wherein the anode and the cathode further comprise silica nanoparticles/laponite, and
wherein the hydrogel electrolyte is in electrochemical contact with the biocompatible anode and the biocompatible cathode;
b. a power source comprising a plurality of electrodes comprising a graphene hydrogel and laponite, the biocompatible conductive hydrogel electrolyte wherein each of the plurality of electrodes is in electrochemical contact with a biocompatible conductive hydrogel electrolyte, wherein the biocompatible electrochemical cell and the power source are in electronic communication with each other; and wherein each biocompatible conductive hydrogel electrolyte is independently an electrically conductive hydrogel comprising a biopolymer backbone to which an ionic liquid side chain is conjugated.

Embodiment 26 provides the device of embodiment 25, wherein the biopolymer backbone comprises a biopolymer selected from the group consisting of gelatin, gelatin methacrylate, elastin, hyaluronic acid (HA), alginate, polyethylene glycol (PEG), 2-hydroxyethyl methacrylate (HeMA), poly(ethylene glycol) diacrylate (PEGDA), and poly glycerol sebacate (PGS).

Embodiment 27 provides the device of any one of embodiments 25-26, wherein the ionic liquid side chain comprises choline.

Embodiment 28 provides the device of any one of embodiments 25-27, wherein the ionic liquid side chain is selected from the group consisting of choline acrylate, choline acetate, choline itaconate, choline salicylate, and mixtures thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An implantable oxygen generating device comprising:
   a. an oxygen generating, biocompatible electrochemical cell,
      wherein the electrochemical cell comprises a biocompatible cathode, a biocompatible anode, and a biocompatible hydrogel electrolyte, and
      wherein the hydrogel electrolyte is in electrochemical contact with the anode and the cathode of the cell;
   b. a biocompatible power source,
      wherein the power source is a supercapacitor comprising a plurality of biocompatible electrodes and a biocompatible hydrogel electrolyte, and
      wherein the hydrogel electrolyte is in electrochemical contact with each of the plurality of the biocompatible electrodes of the power source;
      wherein the biocompatible hydrogel electrolyte in the cell and the biocompatible hydrogel electrolyte in the power source are independently an electrically conductive hydrogel comprising a biopolymer backbone to which an ionic liquid side chain is conjugated; and
      wherein the electrochemical cell is in electronic communication with the power source.

2. The device of claim 1, wherein the biopolymer backbone comprises a biopolymer selected from the group consisting of gelatin, gelatin methacrylate, elastin, hyaluronic acid (HA), alginate, polyethylene glycol (PEG), 2-hydroxyethyl methacrylate (HeMA), poly(ethylene glycol) diacrylate (PEGDA), and poly glycerol sebacate (PGS).

3. The device of claim 1, wherein the hydrogel electrolyte comprises about 10% to about 20% (w/v) of the biopolymer backbone.

4. The device of claim 1, wherein the ionic liquid side chain comprises choline.

5. The device of claim 1, wherein at least one ionic liquid side chain is selected from the group consisting of choline acrylate, choline acetate, choline itaconate, choline salicylate, and any mixtures thereof.

6. The device of claim 1, wherein the hydrogel electrolyte comprises about 0.1% to about 20% (w/v) of at least one ionic liquid side chain.

7. The device of claim 1, wherein the hydrogel electrolyte further comprises a photoinitiator selected from the group consisting of lithium phenyl-2,4,6 trimethylbenzoylphosphinate (LAP), eosin Y, 2-Hydroxy-2-methylpropiophenone, 2-Methyl-4'-(methylthio)-2-morpholinopropiophenone, and 2-Hydroxy-4'-(2-hydroxyethoxy)-2-methylpropiophenone.

8. The device of claim 7, wherein the hydrogel electrolyte comprises about 0.1% to about 1% (w/v) of at least one photoinitiator.

9. The device of claim 1, wherein the hydrogel electrolyte in the electrochemical cell further comprises a biological cell.

10. The device of claim 9, wherein the biological cell is selected from the group consisting of mesenchymal stem cell (MSC), cardiomyocyte, and cardiac fibroblast.

11. The device of claim 1, wherein the electrochemical cell comprises reticular networks of the hydrogel electrolyte.

12. The device of claim 11, wherein the reticular networks form a grid-like pattern.

13. The device of claim 1, wherein the biocompatible anode and the biocompatible cathode each independently comprise at least one material selected from the group consisting of graphene hydrogel, cobalt, zinc, silicon nanoparticles, graphene oxide, magnesium, iron, cobalt phosphate, nickel, nickel phosphate, a combination of nickel and phosphate, and a combination of nickel phosphate and cobalt phosphate.

14. The device of claim 1, wherein the biocompatible anode and biocompatible cathode each comprise cobalt phosphate, graphene hydrogel, and optionally silica nanoparticle/laponite.

15. The device of claim 1, wherein the plurality of electrodes comprises graphene hydrogel.

16. The device of claim 15, wherein the plurality of electrodes further comprises silica nanoparticles/laponite.

17. The device of claim 1, wherein the biocompatible anode and biocompatible cathode each independently comprise about 1% to about 5% (w/v) of cobalt phosphate.

18. The device of claim 1, wherein the device has at least one of the following characteristics: is biodegradable, is biocompatible, is operational at about neutral pH.

19. The device of claim 1, wherein the electrochemical cell and the power source are 3D-printed.

20. The device of claim 1, wherein the power source comprises an interdigitated structure comprising the hydrogel electrolyte and the plurality of biocompatible electrodes.

21. A method of treating a tissue injury in a subject, the method comprising:
    subcutaneously implanting the device of claim 1 into the subject, wherein the device is implanted on, near, or in close proximity to the tissue injury.

22. The method of claim 21, wherein the tissue injury is at least one selected from the group consisting of an ischemic reperfusion injury, muscle injury, pancreatic tissue injury, and neural tissue injury.

23. An oxygen generating biocompatible device comprising
   a. a biocompatible electrochemical cell comprising a graphene hydrogel/cobalt-phosphorous (GH/Co—P) alloy cathode, a graphene hydrogel/cobalt phosphate (GH/CoP$_i$) anode, and a biocompatible, conductive hydrogel electrolyte, wherein the anode and the cathode further comprise silica nanoparticles/laponite, and wherein the hydrogel electrolyte is in electrochemical contact with the biocompatible anode and the biocompatible cathode;

b. a power source comprising a plurality of electrodes comprising a graphene hydrogel and laponite, the biocompatible conductive hydrogel electrolyte wherein each of the plurality of electrodes is in electrochemical contact with a biocompatible conductive hydrogel electrolyte, wherein the biocompatible electrochemical cell and the power source are in electronic communication with each other; and wherein each biocompatible conductive hydrogel electrolyte is independently an electrically conductive hydrogel comprising a biopolymer backbone to which an ionic liquid side chain is conjugated.

24. The device of claim 23, wherein the biopolymer backbone comprises a biopolymer selected from the group consisting of gelatin, gelatin methacrylate, elastin, hyaluronic acid (HA), alginate, polyethylene glycol (PEG), 2-hydroxyethyl methacrylate (HeMA), poly(ethylene glycol) diacrylate (PEGDA), and poly glycerol sebacate (PGS).

25. The device of claim 23, wherein the ionic liquid side chain comprises choline.

26. The device of claim 23, wherein the ionic liquid side chain is selected from the group consisting of choline acrylate, choline acetate, choline itaconate, choline salicylate, and mixtures thereof.

* * * * *